United States Patent [19]
Livingston et al.

[11] Patent Number: 5,962,315
[45] Date of Patent: *Oct. 5, 1999

[54] DNA ENCODING P107 TUMOR SUPPRESSOR AND RELATED POLYPEPTIDES

[75] Inventors: David M. Livingston; Mark E. Ewen, both of Brookline, Mass.

[73] Assignee: Dana-Farber Cancer Institute, Boston, Mass.

[*] Notice: This patent is subject to a terminal disclaimer.

[21] Appl. No.: 08/152,721

[22] Filed: Nov. 15, 1993

Related U.S. Application Data

[62] Division of application No. 07/708,962, May 31, 1991, Pat. No. 5,262,321.

[51] Int. Cl.$^6$ ............................. C12N 5/10; C12N 15/63; C12N 15/12
[52] U.S. Cl. ..................... 435/325; 435/320.1; 536/23.5; 536/24.3
[58] Field of Search ............................... 536/23.5, 24.31, 536/23.2, 24.3; 435/320.1, 252.3, 252.33, 325

[56] References Cited

U.S. PATENT DOCUMENTS 5,262,321  11/1993  Livingston et al. ..................... 435/325

FOREIGN PATENT DOCUMENTS 0 259 031  3/1988  European Pat. Off. .
0 390 323  10/1990  European Pat. Off. .

OTHER PUBLICATIONS

Mark E. Ewen et al., Molecular Cloning, Chromosomal Mapping, and Expression of the cDNA for p107, a Retinoblastoma Gene Product–Related Protein, Sep. 20, 1991, Cell, vol. 66:1155–1164.

Peter Whyte et al., Cellular Targets for Transformation by the Adenovirus E1A Proteins, Cell, Jan. 13, 1989, vol. 56:67–75.

Ed Harlow et al., Association of Adenovirus Early–Region 1A Proteins with Cellular Polypeptides, May 1986, Molecular and Cellular Biology, vol. 6, No. 5:1579–1589.

Mark E. Ewen et al., An N–Terminal Transformation–Governing Sequence of SV40 Large T Antigen Contributes to the Binding of Both p110$^{Rb}$ and a Second Cellular Protein, p120, Jul. 28, 1989, Cell, vol. 58:257–267.

Kenneth Jacobs et al., Isolation and Characterization of Genomic and cDNA Clones of Human Erythropoietin, Feb. 28, 1985, Nature, vol. 313:806–810.

Nicholas Dyson et al., The Cellular 107K Protein That Binds to Adenovirus E1A Also Associates with the Large T Antigens of SV40 and JC Virus, Jul. 28, 1989, Cell, vol. 58:249–255.

Yeung et al., "The Retinoblastoma–Related Gene, RB2, Maps to Human Chromosome 16q12 and rat Chromosome 19", Oncogene 8:3465–8, 1993.

Xavier Mayol et al., "Cloning Of A New Member Of The Retinoblastoma Gene Family (pRb2) Which Binds To The E1A Transforming Domain", Oncogene 1993 Sep., 8(9):2561–6.

Lee et al. (1987), Science 235: 1394–1399.

*Primary Examiner*—George C. Elliott
*Assistant Examiner*—John S. Brusca
*Attorney, Agent, or Firm*—Choate, Hall & Stewart; Sam Pasternack; Brenda H. Jarrell

[57] ABSTRACT

A cDNA encodes p107; a cell contains recombinant p107-encoding DNA; and substantially all of the cells of a nonhuman mammal contain recombinant p107-encoding DNA. Also, a method for diagnosing a condition of tumorigenicity in a subject, includes the steps of obtaining a tissue sample from the subject and detecting the presence of non wild-type p107-encoding gene in the sample, or detecting the absence of wild-type p107-encoding gene in the sample; or extracting DNA from the sample and detecting the presence of non wild-type p107-encoding gene or the absence of wild-type p107-encoding gene in the DNA. Also, a nucleic acid probe is complementary to a portion of a human mutant p107 gene.

24 Claims, 7 Drawing Sheets

```
  1 GTAATATTCAAAAAATATGAGCCAATTTTTTAGATATATTCAAAAATCCATATGAAGAACCACCAAGTTACCACGAAGCCGGAAGCAG
 (1)  V  I  F  K  K  Y  E  P  I  E  F  L  D  I  F  Q  N  P  Y  E  E  P  P  K  L  P  R  S  R  K  Q

91 AGGAGGATTCCTGCAGTGTTAAGGATCTGTTTAATTCTGTTGGACACTTTTTGTTTATACTAAGGGTAATTCTTGTTATACTAAGGGTAATTTCGGATGATTGGGGAT
(31)  R  R  I  P  C  S  V  K  D  L  F  N  F  C  W  T  L  F  V  Y  T  K  G  N  E  R  M  I  G  D

181 GACTTAGTAAACTCTTATCATTACTTCTATGCTCTGGATCTGATTTTTGCCAATGCGATTATGTGCCCAAATAGACAAGACTGCTA
(61)  D  L  V  N  S  Y  H  L  L  C  C  L  D  L  I  F  A  N  A  I  M  C  P  N  R  Q  D  L  L

271 AATCCATCATTTAAAGGTTACCATCTGATTTTCATACGGCTTCTGACTTTACGGTTAAGCCACCCTGCATTGCTCTGTACTGTGT
(91)  N  P  S  F  K  G  L  P  S  D  F  H  T  A  D  F  T  A  S  E  E  P  P  C  I  I  A  V  L  C

361 GAACTGCATGATGGACTTCTGTAGAAGCAAAGGAATAAAGGAGCACTACTTTAAGCCTTACATATATTTCAAACTCTTTGACAGGAAGATA
(121) E  L  H  D  G  L  L  V  E  A  K  G  I  K  E  H  Y  F  K  P  Y  I  S  K  L  F  D  R  K  I

451 TTAAAGGAGAATGCCTCCTGGACCTTTCAAGTTTTACTGATAATAGCAAAGCAGTGAATAAGGAGTATGAAGAGTATGTTCTAACTGTT
(151) L  K  G  E  C  L  L  D  L  S  S  F  T  D  N  S  K  A  V  N  K  E  Y  E  E  Y  V  L  T  V

541 GGTGATTTTGATGAGAGGATCTTTTTGGGAGCAGACGCAGAGAAGAGGAAATTGAACACCTCGAAAGTTCACTCGTGACACCCATTAGGG
(181) G  D  F  D  E  R  I  F  L  G  A  D  A  E  E  E  I  G  T  P  R  K  F  T  R  D  T  P  L  G

631 AAACTGACAGCACAGGCTAATGTGGAGTATAACCTTCAACAGCACTTTGAAAAAAAGGTCATTTGCACCTTCTACCCCACTGACCGGA
(211) K  L  T  A  Q  A  N  V  E  Y  N  L  Q  Q  H  F  E  K  K  R  S  F  A  P  S  T  P  L  T  G

721 CGGAGATATTTACGAGAAAGAAGCAGTCATTACTCCTGTTGCATCAGCCACCCAAAGTGTGAGCCGGTTACAGAGTATTGTGGCTGGT
(241) R  R  Y  L  R  E  K  E  A  V  I  T  P  V  A  S  A  T  Q  S  V  S  R  L  Q  S  I  V  A  G

811 CTGAAAAATGCACCAAGTGACCAACTTATAAATATTTTGAATCTTGTGTGCCGTAATCCTGTGGAAAACATTATGAAAATACTAAAAGGA
(271) L  K  N  A  P  S  D  Q  L  I  N  I  F  E  S  C  V  R  N  P  V  E  N  I  M  K  I  L  K  G
```

FIG. 1A

```
 901  ATAGGAGAGACTTTCTGTCAACACTACTATACTCAATCAACAGATGAACAGCCAGGATCTCACATAGACTTTGCTGTAAACAGACTAAAGCTG
(301)  I  G  E  T  F  C  Q  H  Y  T  Q  S  T  D  E  Q  P  G  S  H  I  D  F  A  V  N  R  L  K  L

991  GCAGAAATTTTGTATTATAAATACTAGAGACTGTAATGGTTCAGGAAACAGAAGACTTCATGGAATGGACATGTCAGTTCTTTTAGAG
(331)  A  E  I  L  Y  Y  K  I  L  E  T  V  M  V  Q  E  T  R  R  L  H  G  M  D  M  S  V  L  L  E

1081  CAAGATATATTTCATCGTCTCCTGATGGCTTGTCCTGTTGTTTGGAAATTGTGCTCTTTGCCTATAGCTCACCTCGTACTTTTCCTTGATTATT
(361)  Q  D  I  F  H  R  S  L  M  A  C  C  L  E  I  V  L  F  A  Y  S  S  P  R  T  F  P  W  I  I

1171  GAAGTTCTCAACTTGCAACCATTTTACTTTTATAAGGTTATTGAGGTGGTGATCCGCTCAGAAGAGGGCTCTCAAGGACATGGTGAAA
(391)  E  V  L  N  L  Q  P  F  Y  F  Y  K  V  I  E  V  V  I  R  S  E  E  G  L  S  R  D  M  V  K

1261  CACCTAAACAGCATTGAAGAACAGATTTTGGAGAGTTTAGCATGGAGTCACGATTCTGCACTGTGGGAGAGCTCTCCAGGTTTCTGCAAAC
(421)  H  L  N  S  I  E  E  Q  I  L  E  S  L  A  W  S  H  D  S  A  L  W  E  A  L  Q  V  S  A  N

1351  AAAGTTCCTACCTGTGAAGAAGTTATATTCCCAAATAACTTTGAAACAGGAAATGTGCAGGAGACATCTTCCCTGATGCCA
(451)  K  V  P  T  C  E  E  V  I  F  P  N  N  F  E  T  G  N  G  G  N  V  Q  G  H  L  P  L  M  P

1441  ATGTCTCCTAATGCACCCAAGAGTCAAGGAAGTTCGAACTGACAGTGGGAGTCTTCGACGAGATATGCAACCATTGTCTCCAATTTCT
(481)  M  S  P  L  M  H  P  R  V  K  E  V  R  T  D  S  G  S  L  R  R  D  M  Q  P  L  S  P  I  S

1531  GTCCATGAACGCTACAGTTCCTCCACCGCAGGAGTGCTAAGAGAAGACTCTTGGAGAGACCCCCAAAGAAATGCTTATGGACAAG
(511)  V  H  E  R  Y  S  S  P  T  A  G  S  A  K  R  R  L  F  G  E  D  P  P  K  E  M  L  M  D  K

1621  ATCATAACGAGGAACAAAATTGAAAATGTATCAATTTTACCTGGTCAAACTCTTCTA
(541)  I  I  T  E  G  T  K  L  K  I  A  P  S  S  I  T  A  E  N  V  S  I  L  P  G  Q  T  L  L

1711  ACAATGGCCACAGCCCCAGTAACAGGAACACAGGACATAAAGTTACAATTCCATTACATGGTCGCAAATGATGCTGGAGAGATCACA
(571)  T  M  A  T  A  P  V  T  G  T  T  G  H  K  V  T  I  P  L  H  G  V  A  N  D  A  G  E  I  T

1801  CTGATACCTCTTTCCATGAATACAAATCAGGAGTCAAGAGTCAAAGTAAGTCCTGTATCACTTACTCTCATTAATTGGTGCTTCTCCA
(601)  L  I  P  L  S  M  N  T  N  Q  E  S  K  V  K  S  P  V  S  L  T  A  H  S  L  I  G  A  S  P
```

FIG. 1B

```
1891       AACAGAGACCAATCTGACTAAAGCACAAGAGTACATTCAACTGGAATAAACAGGCCAAAGAGAACTGGGTCCTTAGCACTATTTTACAGA
(631)       K  Q  T  N  L  T  K  A  Q  E  V  H  S  T  G  I  N  R  P  K  R  T  G  S  L  A  L  F  Y  R

1981       AAGGTCTATCATTTGGCAAGTGTACGCTTACGCTGTATCTGATCTATGTTCAAATGAGTTCAAAGGAAGATATGGACGTGT
(661)       K  V  Y  H  L  A  S  V  R  L  R  D  L  C  L  K  L  D  V  S  N  E  L  R  R  K  I  W  T  C

2071       TTTGAATTCACTTTAGTTCACTGTCCTGATCTAATGAAAGACAGGCATTTGGATCAGCTCCTCCTTTGTGCCTTTTATATCATGGCAAAG
(691)       F  E  F  T  L  V  H  C  P  D  L  M  K  D  R  H  L  D  Q  L  L  L  C  A  F  Y  I  M  A  K

2161       GTAACAAAAGAAGAAAGAACTTTTCAAGAATTTATGAAAATTATGAAGTCACGTATATAGAAGTGTTCTG
(721)       V  T  K  E  E  R  T  F  Q  E  I  M  K  S  Y  R  N  Q  P  Q  A  N  S  H  V  Y  R  S  V  L

2251       CTGAAAAGTATTCCAAGAGAAGTTGTGGCATATAATAAAAATATAAATGATGACTTTGAAATGATAGATTGTGACTTAGAAGATGCTACA
(751)       L  K  S  I  P  R  E  V  V  A  Y  N  K  N  I  N  D  D  F  E  M  I  D  C  D  L  E  D  A  T

2341       AAAACACCTGACTGTTCCAGTGGACCAGTGGTCAAGGAAGAAGAAGTGATCTTATAAAATTTTACAATACAATATATGTAGGAAGAGTGAAG
(781)       K  T  P  D  C  S  S  G  P  V  K  E  E  R  S  D  L  I  K  F  Y  N  T  I  Y  V  G  R  V  K

2431       TCATTTGCACTGAAATACGACTTGGCGAATCAGGATCATATGATGGATGCTCCACCACTCTCTCCTTTCCACATTAAACAACAGCCA
(811)       S  F  A  L  K  Y  D  L  A  N  Q  D  H  M  M  D  A  P  P  L  S  P  F  P  H  I  K  Q  Q  P

2521       GGCTCACCACGCCGCATTTCCCAGCACTCCATTTATATTCCCGCACAAGAATGGGTCAGCCTTACACCAAGAAGCCTCTGCTG
(841)       G  S  P  R  R  I  S  Q  Q  H  S  I  Y  I  S  P  H  K  N  G  S  G  L  T  P  R  S  A  L  L

2611       TACAAGTTCAATGGCAGCCCTTCTAAGAGTTTGAAAGATATCAACAACATGATAAGGCAAGGTGAGCAAGAACCAAGAAGGCGAGTAATA
(871)       Y  K  F  N  G  S  P  S  K  S  L  K  D  I  N  N  M  I  R  Q  G  E  Q  R  T  K  K  R  V  I

2701       GCCATCGATAGTGATGCAGAATCCCCTGCCAAACGCGTCTGTCAAGAAAATGATGACGTTTTACTGAAACGACTACAGGATGTTGTCAGT
(901)       A  I  D  S  D  A  E  S  P  A  K  R  V  C  Q  E  N  D  D  V  L  L  K  R  L  Q  D  V  V  S

2791       GAAAGAGCAAATCATTAA
(931)       E  R  A  N  H  @
```

FIG. 1C

REGION 1  N TERMINAL HOMOLOGY

```
p107   40  LFNFCWTLFVYTKGNFRMIGDDLVNSYHLLICCLD  74
            ** | *| ||  * |||| |**|*|| ||
RB    190  VLKVSWITFLLAKGEVLQMEDDLVISFQLMLCVLD 224
```

DOMAIN A HOMOLOGY

REGION 2

```
p107  252  TPVASATQSVSRLQSIVAGLKNAPSDQLINIFESCVRNPVENIMKILKGIGETFCQHY 309
            |||    * | * *||*|| | |   ||| |*|  |*| | **
RB    373  TPVRTVMNTIQQLMMILNSASDQPSENLISYFNNCTVNPKESILKRVKDIGYIFKEKF 430
```

REGION 3

```
p107  327  RLKLAEILYYKILETVMQETRRLHGMDMSVLLEQDIFHRSLMACCLEIVLFAYS 381
            |  |||  |||***| ** |   * | |  *|| ||*|| ||*| ||
RB    445  RYKLGVRLYYRVMESMLKSEEERLSIQNFSKLLNDNIFHMSLLACALEVVMATYS 499
```

REGION 4

```
p107  386  FPWIIEVLNLQPFYFYKVIEVVIRSEEGLSRDMVKHLNSIEEQILESLAWSHDSALWEALQVSANK 451
            |||* ||||  |  | |||||   |*|  |  | |*|*||| ||  |*|||  || |   | **
RB    514  FPWILNVLNLKAFDFYKVIESFIKAEGNLTREMIKHLERCEHRIMESLAWLSDSPLFDLIKQSKDR 579
```

DOMAIN B HOMOLOGY

REGION 5

```
p107  648  RPKRTGSLALFYRKVYHLASVRLRDICLCKL 677
            *| * || ||*|||***|| *|| || *|
RB    640  KPLKSTSLSLFYKKVYRLAYLRLNTLCERL  669
```

REGION 6

```
p107  682  ELRRKIWTCFEFTLVHCPDLMKDRHLDQLLLCAFYIMAKVTKEERTFQEIMKSYRNQPQANSHVYRSVLLK 752
            || * ||| |* || * *||||||||***|  | *| * |* |  | | *** ||*| ** ||| |*|
RB    675  ELEHIIWTLFQHTLQNEYELMRDRHLDQIMMCSMYGICKVKNIDLKFKIIVTAYKDLPHAVQETFKRVLIK 745
```

REGION 7

```
p107  797  LIKFYNTIYVGRVKSFALKY 816
            *|  | *** ||  ||
RB    752  IIVFYNSVFMQRLKTNILQY 771
```

FIG. 2A

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
      (A) LENGTH: 2808 base pairs
      (B) TYPE: nucleic acid
      (C) STRANDEDNESS: both
      (D) TOPOLOGY: linear (ii) MOLECULE TYPE: cDNA (iii) HYPOTHETICAL: NO (iv) ANTI-SENSE: NO (vii) IMMEDIATE SOURCE:
      (B) CLONE: cDNA encoding p107

(xi) SEQUENCE DESCRIPTION: SEQ ID NO:1:

```
GTAATATTCA AAAAATATGA GCCAATTTTT TTAGATATAT TTCAAAATCC ATATGAAGAA      60

CCACCAAAGT TACCACGAAG CCGGAAGCAG AGGAGGATTC CTTGCAGTGT TAAGGATCTG     120

TTTAATTTCT GTTGGACACT TTTTGTTTAT ACTAAGGGTA ATTTTCGGAT GATTGGGGAT     180

GACTTAGTAA ACTCTTATCA TTTACTTCTA TGCTGCTTGG ATCTGATTTT TGCCAATGCG     240

ATTATGTGCC CAAATAGACA AGACTTGCTA AATCCATCAT TTAAAGGTTT ACCATCTGAT     300
```

-continued

| | |
|---|---|
| TTTCATACTG CTGACTTTAC GGCTTCTGAA GAGCCACCCT GCATCATTGC TGTACTGTGT | 360 |
| GAACTGCATG ATGGACTTCT CGTAGAAGCA AAAGGAATAA AGGAGCACTA CTTTAAGCCA | 420 |
| TATATTTCAA AACTCTTTGA CAGGAAGATA TTAAAAGGAG AATGCCTCCT GGACCTTTCA | 480 |
| AGTTTTACTG ATAATAGCAA AGCAGTGAAT AAGGAGTATG AAGAGTATGT TCTAACTGTT | 540 |
| GGTGATTTTG ATGAGAGGAT CTTTTTGGGA GCAGACGCAG AAGAGGAAAT TGGAACACCT | 600 |
| CGAAAGTTCA CTCGTGACAC CCCATTAGGG AAACTGACAG CACAGGCTAA TGTGGAGTAT | 660 |
| AACCTTCAAC AGCACTTTGA AAAAAAAGG TCATTTGCAC CTTCTACCCC ACTGACCGGA | 720 |
| CGGAGATATT TACGAGAAAA AGAAGCAGTC ATTACTCCTG TTGCATCAGC CACCCAAAGT | 780 |
| GTGAGCCGGT TACAGAGTAT TGTGGCTGGT CTGAAAAATG CACCAAGTGA CCAACTTATA | 840 |
| AATATTTTTG AATCTTGTGT GCGTAATCCT GTGGAAAACA TTATGAAAAT ACTAAAAGGA | 900 |
| ATAGGAGAGA CTTTCTGTCA ACACTATACT CAATCAACAG ATGAACAGCC AGGATCTCAC | 960 |
| ATAGACTTTG CTGTAAACAG ACTAAAGCTG GCAGAAATTT TGTATTATAA AATACTAGAG | 1020 |
| ACTGTAATGG TTCAGGAAAC ACGAAGACTT CATGGAATGG ACATGTCAGT TCTTTTAGAG | 1080 |
| CAAGATATAT TTCATCGTTC CTTGATGGCT TGTTGTTTGG AAATTGTGCT CTTTGCCTAT | 1140 |
| AGCTCACCTC GTACTTTTCC TTGGATTATT GAAGTTCTCA ACTTGCAACC ATTTTACTTT | 1200 |
| TATAAGGTTA TTGAGGTGGT GATCCGCTCA GAAGAGGGGC TCTCAAGGGA CATGGTGAAA | 1260 |
| CACCTAAACA GCATTGAAGA ACAGATTTTG GAGAGTTTAG CATGGAGTCA CGATTCTGCA | 1320 |
| CTGTGGGAGG CTCTCCAGGT TTCTGCAAAC AAAGTTCCTA CCTGTGAAGA AGTTATATTC | 1380 |
| CCAAATAACT TGAAACAGG AAATGGAGGA AATGTGCAGG GACATCTTCC CCTGATGCCA | 1440 |
| ATGTCTCCTC TAATGCACCC AAGAGTCAAG GAAGTTCGAA CTGACAGTGG GAGTCTTCGA | 1500 |
| AGAGATATGC AACCATTGTC TCCAATTTCT GTCCATGAAC GCTACAGTTC TCCTACCGCA | 1560 |
| GGGAGTGCTA AGAAGACT CTTTGGAGAG GACCCCCCAA AGGAAATGCT TATGGACAAG | 1620 |
| ATCATAACAG AAGGAACAAA ATTGAAAATC GCTCCTTCTT CAAGCATTAC TGCTGAAAAT | 1680 |
| GTATCAATTT TACCTGGTCA AACTCTTCTA ACAATGGCCA CAGCCCCAGT AACAGGAACA | 1740 |
| ACAGGACATA AAGTTACAAT TCCATTACAT GGTGTCGCAA ATGATGCTGG AGAGATCACA | 1800 |
| CTGATACCTC TTTCCATGAA TACAAATCAG GAGTCCAAAG TCAAGAGTCC TGTATCACTT | 1860 |
| ACTGCTCATT CATTAATTGG TGCTTCTCCA AAACAGACCA ATCTGACTAA AGCACAAGAG | 1920 |
| GTACATTCAA CTGGAATAAA CAGGCCAAAG AGAACTGGGT CCTTAGCACT ATTTTACAGA | 1980 |
| AAGGTCTATC ATTTGGCAAG TGTACGCTTA CGTGATCTAT GTCTAAAACT GGATGTTTCA | 2040 |
| AATGAGTTAC GAAGGAAGAT ATGGACGTGT TTTGAATTCA CTTTAGTTCA CTGTCCTGAT | 2100 |
| CTAATGAAAG ACAGGCATTT GGATCAGCTC CTCCTTTGTG CCTTTTATAT CATGGCAAAG | 2160 |
| GTAACAAAAG AAGAAAGAAC TTTTCAAGAA ATTATGAAAA GTTATAGGAA TCAGCCCCAA | 2220 |
| CGTAATAGTC ACGTATATAG AAGTGTTCTG CTGAAAAGTA TTCCAAGAGA AGTTGTGGCA | 2280 |
| TATAATAAAA ATATAAATGA TGACTTTGAA ATGATAGATT GTGACTTAGA AGATGCTACA | 2340 |
| AAAACACCTG ACTGTTCCAG TGGACCAGTG AAAGAGGAAA GAAGTGATCT TATAAAATTT | 2400 |
| TACAATACAA TATATGTAGG AAGAGTGAAG TCATTTGCAC TGAAATACGA CTTGGCGAAT | 2460 |
| CAGGACCATA TGATGGATGC TCCACCACTC TCTCCTTTTC CACATATTAA ACAACAGCCA | 2520 |
| GGCTCACCAC GCCGCATTTC CCAGCAGCAC TCCATTTATA TTTCCCCGCA CAAGAATGGG | 2580 |
| TCAGGCCTTA CACCAAGAAG CGCTCTGCTG TACAAGTTCA ATGGCAGCCC TTCTAAGAGT | 2640 |
| TTGAAAGATA TCAACAACAT GATAAGGCAA GGTGAGCAGA GAACCAAGAA GCGAGTAATA | 2700 |

```
GCCATCGATA GTGATGCAGA ATCCCCTGCC AAACGCGTCT GTCAAGAAAA TGATGACGTT    2760

TTACTGAAAC GACTACAGGA TGTTGTCAGT GAAAGAGCAA ATCATTAA                2808
```

(2) INFORMATION FOR SEQ ID NO:2:

(i) SEQUENCE CHARACTERISTICS:
        (A) LENGTH: 935 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vii) IMMEDIATE SOURCE:
        (B) CLONE: p107 amino acid sequence (xi) SEQUENCE DESCRIPTION: SEQ ID NO:2:

```
Val Ile Phe Lys Lys Tyr Glu Pro Ile Phe Leu Asp Ile Phe Gln Asn
 1               5                  10                  15

Pro Tyr Glu Glu Pro Pro Lys Leu Pro Arg Ser Arg Lys Gln Arg Arg
            20                  25                  30

Ile Pro Cys Ser Val Lys Asp Leu Phe Asn Phe Cys Trp Thr Leu Phe
        35                  40                  45

Val Tyr Thr Lys Gly Asn Phe Arg Met Ile Gly Asp Asp Leu Val Asn
    50                  55                  60

Ser Tyr His Leu Leu Leu Cys Cys Leu Asp Leu Ile Phe Ala Asn Ala
65                  70                  75                  80

Ile Met Cys Pro Asn Arg Gln Asp Leu Leu Asn Pro Ser Phe Lys Gly
                85                  90                  95

Leu Pro Ser Asp Phe His Thr Ala Asp Phe Thr Ala Ser Glu Glu Pro
            100                 105                 110

Pro Cys Ile Ile Ala Val Leu Cys Glu Leu His Asp Gly Leu Leu Val
        115                 120                 125

Glu Ala Lys Gly Ile Lys Glu His Tyr Phe Lys Pro Tyr Ile Ser Lys
    130                 135                 140

Leu Phe Asp Arg Lys Ile Leu Lys Gly Glu Cys Leu Leu Asp Leu Ser
145                 150                 155                 160

Ser Phe Thr Asp Asn Ser Lys Ala Val Asn Lys Glu Tyr Glu Glu Tyr
                165                 170                 175

Val Leu Thr Val Gly Asp Phe Asp Glu Arg Ile Phe Leu Gly Ala Asp
            180                 185                 190

Ala Glu Glu Glu Ile Gly Thr Pro Arg Lys Phe Thr Arg Asp Thr Pro
        195                 200                 205

Leu Gly Lys Leu Thr Ala Gln Ala Asn Val Glu Tyr Asn Leu Gln Gln
    210                 215                 220

His Phe Glu Lys Lys Arg Ser Phe Ala Pro Ser Thr Pro Leu Thr Gly
225                 230                 235                 240

Arg Arg Tyr Leu Arg Glu Lys Glu Ala Val Ile Thr Pro Val Ala Ser
                245                 250                 255

Ala Thr Gln Ser Val Ser Arg Leu Gln Ser Ile Val Ala Gly Leu Lys
            260                 265                 270

Asn Ala Pro Ser Asp Gln Leu Ile Asn Ile Phe Glu Ser Cys Val Arg
        275                 280                 285

Asn Pro Val Glu Asn Ile Met Lys Ile Leu Lys Gly Ile Gly Glu Thr
    290                 295                 300
```

```
Phe Cys Gln His Tyr Thr Gln Ser Thr Asp Glu Gln Pro Gly Ser His
305                 310                 315                 320

Ile Asp Phe Ala Val Asn Arg Leu Lys Leu Ala Glu Ile Leu Tyr Tyr
                325                 330                 335

Lys Ile Leu Glu Thr Val Met Val Gln Glu Thr Arg Arg Leu His Gly
            340                 345                 350

Met Asp Met Ser Val Leu Leu Glu Gln Asp Ile Phe His Arg Ser Leu
        355                 360                 365

Met Ala Cys Cys Leu Glu Ile Val Leu Phe Ala Tyr Ser Ser Pro Arg
    370                 375                 380

Thr Phe Pro Trp Ile Ile Glu Val Leu Asn Leu Gln Pro Phe Tyr Phe
385                 390                 395                 400

Tyr Lys Val Ile Glu Val Val Ile Arg Ser Glu Glu Gly Leu Ser Arg
                405                 410                 415

Asp Met Val Lys His Leu Asn Ser Ile Glu Glu Gln Ile Leu Glu Ser
            420                 425                 430

Leu Ala Trp Ser His Asp Ser Ala Leu Trp Glu Ala Leu Gln Val Ser
        435                 440                 445

Ala Asn Lys Val Pro Thr Cys Glu Glu Val Ile Phe Pro Asn Asn Phe
    450                 455                 460

Glu Thr Gly Asn Gly Gly Asn Val Gln Gly His Leu Pro Leu Met Pro
465                 470                 475                 480

Met Ser Pro Leu Met His Pro Arg Val Lys Glu Val Arg Thr Asp Ser
                485                 490                 495

Gly Ser Leu Arg Arg Asp Met Gln Pro Leu Ser Pro Ile Ser Val His
            500                 505                 510

Glu Arg Tyr Ser Ser Pro Thr Ala Gly Ser Ala Lys Arg Arg Leu Phe
        515                 520                 525

Gly Glu Asp Pro Pro Lys Glu Met Leu Met Asp Lys Ile Ile Thr Glu
    530                 535                 540

Gly Thr Lys Leu Lys Ile Ala Pro Ser Ser Ile Thr Ala Glu Asn
545                 550                 555                 560

Val Ser Ile Leu Pro Gly Gln Thr Leu Leu Thr Met Ala Thr Ala Pro
                565                 570                 575

Val Thr Gly Thr Thr Gly His Lys Val Thr Ile Pro Leu His Gly Val
            580                 585                 590

Ala Asn Asp Ala Gly Glu Ile Thr Leu Ile Pro Leu Ser Met Met Thr
        595                 600                 605

Asn Gln Glu Ser Lys Val Lys Ser Pro Val Ser Leu Thr Ala His Ser
    610                 615                 620

Leu Ile Gly Ala Ser Pro Lys Gln Thr Asn Leu Thr Lys Ala Gln Glu
625                 630                 635                 640

Val His Ser Thr Gly Ile Asn Arg Pro Lys Arg Thr Gly Ser Leu Ala
                645                 650                 655

Leu Phe Tyr Arg Lys Val Tyr His Leu Ala Ser Val Arg Leu Arg Asp
            660                 665                 670

Leu Cys Leu Lys Leu Asp Val Ser Asn Glu Leu Arg Arg Lys Ile Trp
        675                 680                 685

Thr Cys Phe Glu Phe Thr Leu Val His Cys Pro Asp Leu Met Lys Asp
    690                 695                 700

Arg His Leu Asp Gln Leu Leu Cys Ala Phe Tyr Ile Met Ala Lys
705                 710                 715                 720

Val Thr Lys Glu Glu Arg Thr Phe Gln Glu Ile Met Lys Ser Tyr Arg
```

```
                      725                 730                 735
    Asn Gln Pro Gln Ala Asn Ser His Val Tyr Arg Ser Val Leu Leu Lys
                740                 745                 750

Ser Ile Pro Arg Glu Val Val Ala Tyr Asn Lys Asn Ile Asn Asp Asp
                755                 760                 765

Phe Glu Met Ile Asp Cys Asp Leu Glu Asp Ala Thr Lys Thr Pro Asp
                770                 775                 780

Cys Ser Ser Gly Pro Val Lys Glu Glu Arg Ser Asp Leu Ile Lys Phe
    785                 790                 795                 800

Tyr Asn Thr Ile Tyr Val Gly Arg Val Lys Ser Phe Ala Leu Lys Tyr
                    805                 810                 815

Asp Leu Ala Asn Gln Asp His Met Met Asp Ala Pro Pro Leu Ser Pro
                820                 825                 830

Phe Pro His Ile Lys Gln Gln Pro Gly Ser Pro Arg Arg Ile Ser Gln
                835                 840                 845

Gln His Ser Ile Tyr Ile Ser Pro His Lys Asn Gly Ser Gly Leu Thr
                850                 855                 860

Pro Arg Ser Ala Leu Leu Tyr Lys Phe Asn Gly Ser Pro Ser Lys Ser
    865                 870                 875                 880

Leu Lys Asp Ile Asn Asn Met Ile Arg Gln Gly Glu Gln Arg Thr Lys
                    885                 890                 895

Lys Arg Val Ile Ala Ile Asp Ser Asp Ala Glu Ser Pro Ala Lys Arg
                900                 905                 910

Val Cys Gln Glu Asn Asp Asp Val Leu Leu Lys Arg Leu Gln Asp Val
                915                 920                 925

Val Ser Glu Arg Ala Asn His
                930                 935

(2) INFORMATION FOR SEQ ID NO:3:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: peptide NT65

(xi) SEQUENCE DESCRIPTION: SEQ ID NO:3:

Leu Thr Ala Gln Ala Asn Val Glu Tyr Asn Leu Gln Gln His Phe Glu
1               5                   10                  15
Lys (2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vii) IMMEDIATE SOURCE:
        (B) CLONE: peptide NT85
```

(xi) SEQUENCE DESCRIPTION: SEQ ID NO:4:

Glu Tyr Glu Glu Tyr Val Leu Thr Val Gly Asp Phe Asp Glu
1               5                   10

(2) INFORMATION FOR SEQ ID NO:5:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (vii) IMMEDIATE SOURCE:
            (B) CLONE: peptide NT104

(xi) SEQUENCE DESCRIPTION: SEQ ID NO:5:

Val Thr Ile Pro Leu His Gly Val Ala Asn Asp Ala Gly Glu Ile Thr
1               5                   10                  15

Leu Ile Pro (2) INFORMATION FOR SEQ ID NO:6:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: oligonucleotide (xi) SEQUENCE DESCRIPTION: SEQ ID NO:6:

GAGGCYAATG TGGAGTAYAA CCTGCAGCAG CAYTTTGAGA A                            41

(2) INFORMATION FOR SEQ ID NO:7:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: DNA (genomic)

(vii) IMMEDIATE SOURCE:
            (B) CLONE: oligonucleotide (ix) FEATURE:
            (A) NAME/KEY: misc_feature
            (B) LOCATION: 1..4
            (D) OTHER INFORMATION: /function= "facillitates cloning"

(ix) FEATURE:
            (A) NAME/KEY: misc_feature
            (B) LOCATION: 46
            (D) OTHER INFORMATION: /function= "facilliatates cloning"

(xi) SEQUENCE DESCRIPTION: SEQ ID NO:7:

AATTCTCATC AAGTCGCCCA CTGTCAGCAC ATACTCCTCA TACTCG                       46

(2) INFORMATION FOR SEQ ID NO:8:

(i) SEQUENCE CHARACTERISTICS:

```
        (A) LENGTH: 62 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: oligonucleotide (ix) FEATURE:
        (A) NAME/KEY: misc_feature
        (B) LOCATION: 1..4
        (D) OTHER INFORMATION: /function= "facillitates cloning"

(ix) FEATURE:
        (A) NAME/KEY: misc_feature
        (B) LOCATION: 62
        (D) OTHER INFORMATION: /function= "facillitates cloning"

(xi) SEQUENCE DESCRIPTION: SEQ ID NO:8:

AATTCGGGGA TCAGGGTGAT CTCGCCAGCA TCATTGGCCA GCCATGCAGG GGGATGGTCA       60

CG                                                                    62

(2) INFORMATION FOR SEQ ID NO:9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: oligonucleotide (xi) SEQUENCE DESCRIPTION: SEQ ID NO:9:

GCGCGGATCC GCCACCATGA TTGGGGATGA CTTAG                                 35

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: oligonucleotide (xi) SEQUENCE DESCRIPTION: SEQ ID NO:10:

AGTGGGATCC AATACGACTC ACTATAGG                                         28

(2) INFORMATION FOR SEQ ID NO:11:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vii) IMMEDIATE SOURCE:
        (B) CLONE: region 2 consensus between p107 and RB
```

(xi) SEQUENCE DESCRIPTION: SEQ ID NO:11:

Thr Pro Val Xaa Xaa Xaa Xaa Xaa Xaa Xaa Xaa Leu Xaa Xaa Ile
1               5                  10                  15

Xaa Xaa Xaa Xaa Xaa Xaa Xaa Pro Ser Xaa Xaa Leu Ile Xaa Xaa Phe
            20                  25                  30

Xaa Xaa Cys Xaa Xaa Asn Pro Xaa Glu Xaa Ile Xaa Lys Xaa Xaa Lys
        35                  40                  45

Xaa Ile Gly Xaa Xaa Phe
    50

(2) INFORMATION FOR SEQ ID NO:12:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vii) IMMEDIATE SOURCE:
        (B) CLONE: region 3 consensus between p107 and RB (xi) SEQUENCE DESCRIPTION: SEQ ID NO:12:

Arg Xaa Lys Leu Xaa Xaa Xaa Leu Tyr Tyr Xaa Xaa Xaa Glu Xaa Xaa
1               5                  10                  15

Xaa Xaa Xaa Glu Xaa Xaa Arg Leu Xaa Xaa Xaa Xaa Xaa Ser Xaa Leu
            20                  25                  30

Leu Xaa Xaa Xaa Ile Phe His Xaa Ser Leu Xaa Ala Cys Xaa Leu Glu
        35                  40                  45

Xaa Val Xaa Xaa Xaa Tyr Ser
    50              55

(2) INFORMATION FOR SEQ ID NO:13:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: region 4 consensus between p107 and RB (xi) SEQUENCE DESCRIPTION: SEQ ID NO:13:

Phe Pro Trp Ile Xaa Xaa Val Leu Asn Leu Xaa Xaa Phe Xaa Phe Tyr
1               5                  10                  15

Lys Val Ile Glu Xaa Xaa Ile Xaa Xaa Glu Xaa Xaa Leu Xaa Arg Xaa
            20                  25                  30

Met Xaa Lys His Leu Xaa Xaa Xaa Glu Xaa Xaa Ile Xaa Glu Ser Leu
        35                  40                  45

Ala Trp Xaa Xaa Asp Ser Xaa Leu Xaa Xaa Xaa Xaa Xaa Xaa Ser
    50              55                  60

(2) INFORMATION FOR SEQ ID NO:14:

(i) SEQUENCE CHARACTERISTICS:
    (A) LENGTH: 29 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (vii) IMMEDIATE SOURCE:
    (B) CLONE: region 5 homology between p107 and RB (xi) SEQUENCE DESCRIPTION: SEQ ID NO:14:

```
Pro Xaa Xaa Xaa Xaa Ser Leu Xaa Leu Phe Tyr Xaa Lys Val Tyr Xaa
1               5                   10                  15

Leu Ala Xaa Xaa Arg Leu Xaa Xaa Leu Cys Xaa Xaa Leu
            20                  25
```

(2) INFORMATION FOR SEQ ID NO:15:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: region 6 consensus between p107 and RB (xi) SEQUENCE DESCRIPTION: SEQ ID NO:15:

```
Glu Leu Xaa Xaa Xaa Ile Trp Thr Xaa Phe Xaa Xaa Thr Leu Xaa Xaa
1               5                   10                  15

Xaa Xaa Xaa Leu Met Xaa Asp Arg His Leu Asp Gln Xaa Xaa Xaa Cys
            20                  25                  30

Xaa Xaa Tyr Xaa Xaa Xaa Lys Val Xaa Xaa Xaa Xaa Xaa Phe Xaa
        35                  40                  45

Xaa Ile Xaa Xaa Xaa Tyr Xaa Xaa Xaa Pro Xaa Ala Xaa Xaa Xaa Xaa
    50                  55                  60

Xaa Xaa Xaa Val Leu Xaa Lys
65                  70
```

(2) INFORMATION FOR SEQ ID NO:16:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vii) IMMEDIATE SOURCE:
        (B) CLONE: region 7 consensus between p107 and RB (xi) SEQUENCE DESCRIPTION: SEQ ID NO:16:

```
Ile Xaa Phe Tyr Asn Xaa Xaa Xaa Xaa Xaa Arg Xaa Lys Xaa Xaa Xaa
1               5                   10                  15

Leu Xaa Tyr
```

(2) INFORMATION FOR SEQ ID NO:17:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: p107 region 1

(xi) SEQUENCE DESCRIPTION: SEQ ID NO:17:

```
Leu Phe Asn Phe Cys Trp Thr Leu Phe Val Tyr Thr Lys Gly Asn Phe
1               5                   10                  15

Arg Met Ile Gly Asp Asp Leu Val Asn Ser Tyr His Leu Leu Leu Cys
            20                  25                  30

Cys Leu Asp
        35
```

(2) INFORMATION FOR SEQ ID NO:18:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: RB region 1

(xi) SEQUENCE DESCRIPTION: SEQ ID NO:18:

```
Val Leu Lys Val Ser Trp Ile Thr Phe Leu Leu Ala Lys Gly Glu Val
1               5                   10                  15

Leu Gln Met Glu Asp Asp Leu Val Ile Ser Phe Gln Leu Met Leu Cys
            20                  25                  30

Val Leu Asp
        35
```

(2) INFORMATION FOR SEQ ID NO:19:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:

(B) CLONE: p107 region 2

(xi) SEQUENCE DESCRIPTION: SEQ ID NO:19:

Thr Pro Val Ala Ser Ala Thr Gln Ser Val Ser Arg Leu Gln Ser Ile
1               5                   10                  15

Val Ala Gly Leu Lys Asn Ala Pro Ser Asp Gln Leu Ile Asn Ile Phe
            20                  25                  30

Glu Ser Cys Val Arg Asn Pro Val Glu Asn Ile Met Lys Ile Leu Lys
        35                  40                  45

Gly Ile Gly Glu Thr Phe Cys Gln His Tyr
    50                  55

(2) INFORMATION FOR SEQ ID NO:20:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: RB region 2

(xi) SEQUENCE DESCRIPTION: SEQ ID NO:20:

Thr Pro Val Arg Thr Val Met Asn Thr Ile Gln Gln Leu Met Met Ile
1               5                   10                  15

Leu Asn Ser Ala Ser Asp Gln Pro Ser Glu Asn Leu Ile Ser Tyr Phe
            20                  25                  30

Asn Asn Cys Thr Val Asn Pro Lys Glu Ser Ile Leu Lys Arg Val Lys
        35                  40                  45

Asp Ile Gly Tyr Ile Phe Lys Glu Lys Phe
    50                  55

(2) INFORMATION FOR SEQ ID NO:21:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: p107 region 3

(xi) SEQUENCE DESCRIPTION: SEQ ID NO:21:

Arg Leu Lys Leu Ala Glu Ile Leu Tyr Tyr Lys Ile Leu Glu Thr Val
1               5                   10                  15

Met Val Gln Glu Thr Arg Arg Leu His Gly Met Asp Met Ser Val Leu
            20                  25                  30

Leu Glu Gln Asp Ile Phe His Arg Ser Leu Met Ala Cys Cys Leu Glu
        35                  40                  45

```
Ile Val Leu Phe Ala Tyr Ser
    50              55
```

(2) INFORMATION FOR SEQ ID NO:22:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: RB region 3

(xi) SEQUENCE DESCRIPTION: SEQ ID NO:22:

```
Arg Tyr Lys Leu Gly Val Arg Leu Tyr Tyr Arg Val Met Glu Ser Met
1               5                   10                  15

Leu Lys Ser Glu Glu Glu Arg Leu Ser Ile Gln Asn Phe Ser Lys Leu
            20                  25                  30

Leu Asn Asp Asn Ile Phe His Met Ser Leu Leu Ala Cys Ala Leu Glu
        35                  40                  45

Val Val Met Ala Thr Tyr Ser
    50              55
```

(2) INFORMATION FOR SEQ ID NO:23:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: p107 region 4

(xi) SEQUENCE DESCRIPTION: SEQ ID NO:23:

```
Phe Pro Trp Ile Ile Glu Val Leu Asn Leu Gln Pro Phe Tyr Phe Tyr
1               5                   10                  15

Lys Val Ile Glu Val Val Ile Arg Ser Glu Glu Gly Leu Ser Arg Asp
            20                  25                  30

Met Val Lys His Leu Asn Ser Ile Glu Glu Gln Ile Leu Glu Ser Leu
        35                  40                  45

Ala Trp Ser His Asp Ser Ala Leu Trp Glu Ala Leu Gln Val Ser Ala
    50                  55                  60

Asn Lys
65
```

(2) INFORMATION FOR SEQ ID NO:24:

(i) SEQUENCE CHARACTERISTICS:
        (A) LENGTH: 66 amino acids

```
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
            (B) CLONE: RB region 4

(xi) SEQUENCE DESCRIPTION: SEQ ID NO:24:

Phe Pro Trp Ile Leu Asn Val Leu Asn Leu Lys Ala Phe Asp Phe Tyr
1               5                   10                  15

Lys Val Ile Glu Ser Phe Ile Lys Ala Glu Gly Asn Leu Thr Arg Glu
            20                  25                  30

Met Ile Lys His Leu Glu Arg Cys Glu His Arg Ile Met Glu Ser Leu
            35                  40                  45

Ala Trp Leu Ser Asp Ser Pro Leu Phe Asp Leu Ile Lys Gln Ser Lys
        50                  55                  60

Asp Arg
65

(2) INFORMATION FOR SEQ ID NO:25:

(i) SEQUENCE CHARACTERISTICS:
            (A) LENGTH: 30 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
            (B) CLONE: p107 region 5

(xi) SEQUENCE DESCRIPTION: SEQ ID NO:25:

Arg Pro Lys Arg Thr Gly Ser Leu Ala Leu Phe Tyr Arg Lys Val Tyr
1               5                   10                  15

His Leu Ala Ser Val Arg Leu Arg Asp Leu Cys Leu Lys Leu
            20                  25                  30

(2) INFORMATION FOR SEQ ID NO:26:

(i) SEQUENCE CHARACTERISTICS:
            (A) LENGTH: 30 amino acids
            (B) TYPE: amino acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vii) IMMEDIATE SOURCE:
            (B) CLONE: RB region 5
```

(xi) SEQUENCE DESCRIPTION: SEQ ID NO:26:

Lys Pro Leu Lys Ser Thr Ser Leu Ser Leu Phe Tyr Lys Val Tyr
1               5                   10                  15

Arg Leu Ala Tyr Leu Arg Leu Asn Thr Leu Cys Glu Arg Leu
            20                  25                  30

(2) INFORMATION FOR SEQ ID NO:27:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (v) FRAGMENT TYPE: internal (vii) IMMEDIATE SOURCE:
        (B) CLONE: p107 region 6

(xi) SEQUENCE DESCRIPTION: SEQ ID NO:27:

Glu Leu Arg Arg Lys Ile Trp Thr Cys Phe Glu Phe Thr Leu Val His
1               5                   10                  15

Cys Pro Asp Leu Met Lys Asp Arg His Leu Asp Gln Leu Leu Leu Cys
            20                  25                  30

Ala Phe Tyr Ile Met Ala Lys Val Thr Lys Glu Glu Arg Thr Phe Gln
        35                  40                  45

Glu Ile Met Lys Ser Tyr Arg Asn Gln Pro Gln Ala Asn Ser His Val
    50                  55                  60

Tyr Arg Ser Val Leu Leu Lys
65                  70

(2) INFORMATION FOR SEQ ID NO:28:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: RB region 6

(xi) SEQUENCE DESCRIPTION: SEQ ID NO:28:

Glu Leu Glu His Ile Ile Trp Thr Leu Phe Gln His Thr Leu Gln Asn
1               5                   10                  15

Glu Tyr Glu Leu Met Arg Asp Arg His Leu Asp Gln Ile Met Met Cys
            20                  25                  30

Ser Met Tyr Gly Ile Cys Lys Val Lys Asn Ile Asp Leu Lys Phe Lys
        35                  40                  45

Ile Ile Val Thr Ala Tyr Lys Asp Leu Pro His Ala Val Gln Glu Thr
    50                  55                  60

Phe Lys Arg Val Leu Ile Lys
65                  70

(2) INFORMATION FOR SEQ ID NO:29:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: p107 region 7

(xi) SEQUENCE DESCRIPTION: SEQ ID NO:29:

```
Leu Ile Lys Phe Tyr Asn Thr Ile Tyr Val Gly Arg Val Lys Ser Phe
1               5                   10                  15

Ala Leu Lys Tyr
            20
```

(2) INFORMATION FOR SEQ ID NO:30:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: RB region 7

(xi) SEQUENCE DESCRIPTION: SEQ ID NO:30:

```
Ile Ile Val Phe Tyr Asn Ser Val Phe Met Gln Arg Leu Lys Thr Asn
1               5                   10                  15

Ile Leu Gln Tyr
            20
```

(2) INFORMATION FOR SEQ ID NO:31:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
        (B) CLONE: region 1 consensus between p107 and RB (xi) SEQUENCE DESCRIPTION: SEQ ID NO:31:

```
Trp Xaa Xaa Phe Xaa Xaa Xaa Lys Gly Xaa Xaa Xaa Xaa Xaa Xaa Asp
1               5               10                      15

Asp Leu Val Xaa Ser Xaa Xaa Leu Xaa Leu Cys Xaa Leu Asp
                20              25              30
```

DNA ENCODING P107 TUMOR SUPPRESSOR AND RELATED POLYPEPTIDES

This is divisional application of application Ser. No. 07/708,962 filed May 31, 1991, issued as U.S. Pat. No. 5,262,321 on Nov. 15, 1993, the entire contents of which are corporated herein by reference.

This invention was made in the course of work supported in part by U.S. Government funds, and the government has certain rights in the invention.

BACKGROUND OF THE INVENTION

This invention relates to regulation of tumor suppression.

Tumors form in part as a result of disturbances in the control of cell proliferation. Alteration of one or more events in the cell cycle, particularly relating to cell division and cell differentiation, can lead to loss of control of cell multiplication. Acquisition of tumorigenicity can result from genetic changes that affect such events in the cell cycle. Generally, genetic changes such as point mutations and deletions are expected to result in a loss of function, and a genetic change that leads to tumorigenicity is likely to occur in a gene that plays a role in restraining cell multiplication. Such genes are here referred to as "tumor suppressor" genes.

SV40 large T antigen ("T") can both establish and maintain a neoplastic phenotype in responsive cell populations, and can initiate a series of events that lead to tumor formation in a suitable host. Genetic analysis has revealed a correlation between specific elements of T primary structure and transforming activity. Transformation of primary and established cells by T is dependent on a short stretch of sequence extending from residues about 105 to about 114, and a number of T mutants mapping to the 105 to 114 region have been shown to be defective in transformation.

The 105 to 114 region of T bears primary sequence and predicted secondary structure homology to one of the two transformation controlling domains of the adenovirus E1A protein domain 2, and T 101 to 108 has been shown to substitute functionally for E1A domain 2.

The product "RB" of the retinoblastoma susceptibility gene RB forms a specific complex with E1A, with T, and with E7 encoded by transforming strains of human papilloma virus. RB is a known growth regulating molecule. T-RB complex formation depends on the intact nature of the 105–114 transforming controlling region. E1A-RB complex formation depends primarily on E1A domain 2. The genetics of T-RB binding and E1A-RB binding suggest that T and E1A perform their transforming functions, at least in part, by modulating the, growth regulating function of RB.

Analyses of the RB structural elements which control the T or E1A binding activity of the RB protein reveal the existence of a colinear domain of about 400 residues which alone can bind both T and E1A. Moreover, this region can specifically bind to peptide replicas of the T 105–114 and E1A domain 2 sequences and not to suitable mutant derivatives of T 105–114 or E1A domain 2. This domain of the RB protein has been termed its "pocket", because it acts as a receptacle for two viral proteins which enter it with apparently high affinity. Moreover, the RB pocket is a site for mutations resulting in spontaneous loss of function in RB, resulting in derivatives which are functionally defective in vivo and unable to bind to T or E1A in vitro. These findings suggested that the "pocket" operated, at least in part, by binding one or more cellular proteins and, therefore, that RB function was, in part, to bind to and functionally modulate certain cellular proteins with which T and E1A competed for RB binding.

A set of such cellular proteins has recently been identified in an in vitro binding assay, and all bind only when the T binding function and the E1A binding function of the "pocket" is intact. These data support the hypothesis that at least part of the function of RB is to bind certain cellular proteins.

Domain 2 of E1A and the 105–114 region of T have been shown to form a specific complex with a second cellular protein, p107, and T binding both to RB and to p107 has been shown to be competed by a synthetic peptide spanning the 105 to 114 region in T.

SUMMARY OF THE INVENTION

We have discovered that p107 binds viral proteins and cellular proteins in much the same manner as does RB, and that the p107 sequence (SEQ ID NO:2) includes a binding domain, here termed the "p107 pocket", structurally and functionally similar to the RB pocket. Protein p107 is a tumor suppressor gene product, having cell cycle regulatory activity.

We have purified and characterized p107, and have obtained and fully sequenced a near full length cDNA clone of the p107 gene from human cells. Analysis of the p107 cDNA sequence and of the behavior of its in vitro translated products show that p107 contains a binding domain like the RB pocket, which can perform a T-p107 binding function and a E1A-p107 binding function.

Comparison analysis of the deduced p107 protein sequence reveals a major region of homology with RB extending over 564 residues, that includes the respective RB and p107 pockets. There is very little homology between RB and p107 outside this region. The p107 coding sequences map to 20q 11.2.

A search of protein sequence databases reveals that, like RB, p107 does not substantially resemble other proteins whose sequences are known.

In general, in one aspect, the invention features a cDNA encoding p107 ; and a cell containing recombinant p107-encoding DNA; and a nonhuman mammal substantially all of whose cells contain recombinant p107-encoding DNA. In preferred embodiments the cell or the mammal's cells contain recombinant wild-type p107-encoding DNA. In preferred embodiments the p107-encoding DNA encodes human p107.

In another general aspect, the invention features a method for diagnosing a condition of tumorigenicity in a subject, including the steps of obtaining a tissue sample from the subject and detecting the presence of non wild-type p107-encoding gene in the sample, or detecting the absence of wild-type p107-encoding gene in the sample.

In another general aspect, the invention features a nucleic acid probe complementary to a portion of a human mutant p107 gene.

DESCRIPTION OF PREFERRED EMBODIMENTS

DRAWINGS

FIGS. 1A–1C is a diagram showing the nucleic acid sequence (SEQ ID NO:1) of the nearly complete p107 cDNA and the deduced amino acid sequence (SEQ ID NO:2) of the p107 protein.

Figure 2B:
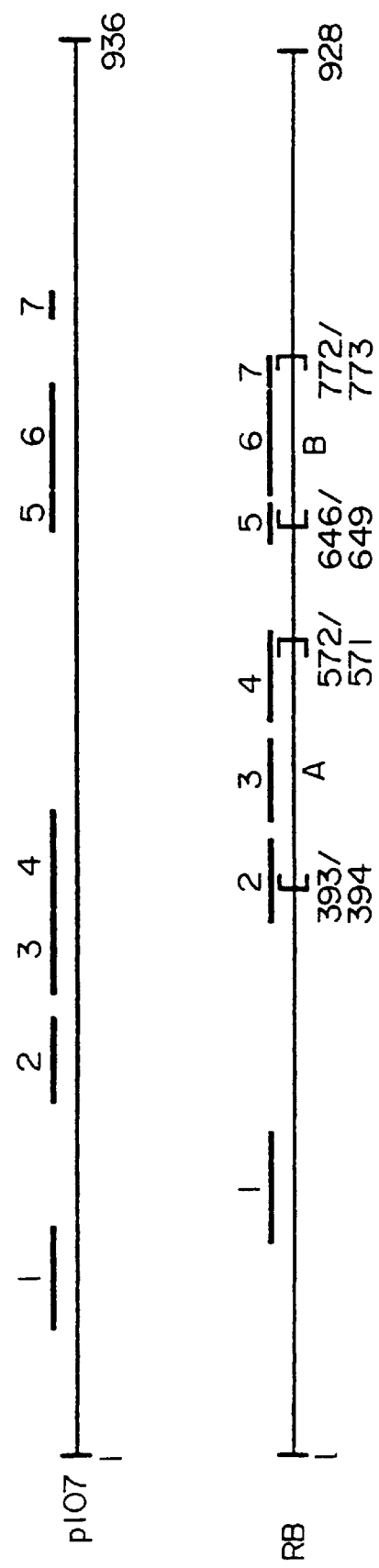
FIG. 2A is a schematic showing the relative positions of seven regions of homology (numbered bars) between the RB and the p107 amino acid sequences. The mapped domains (A, B) of the RB pocket are indicated by brackets with coordinates.

FIG. 2B is a set of diagrams showing the amino acid sequences for the seven regions of homology shown in FIG. 2A. p107 sequences shown in FIG. 2B are presented in the Sequence Listing as SEQ ID NOs.: 17, 19, 21, 23, 25, 27, and 29; RB sequences are SEQ ID NOs.: 18, 20, 22, 24, 26, 28, and 30; consensus sequences are SEQ ID NO.s: 11–16 and 31. Bars indicate identity and stars indicate conservative amino acid substitutions.

Figure 3:
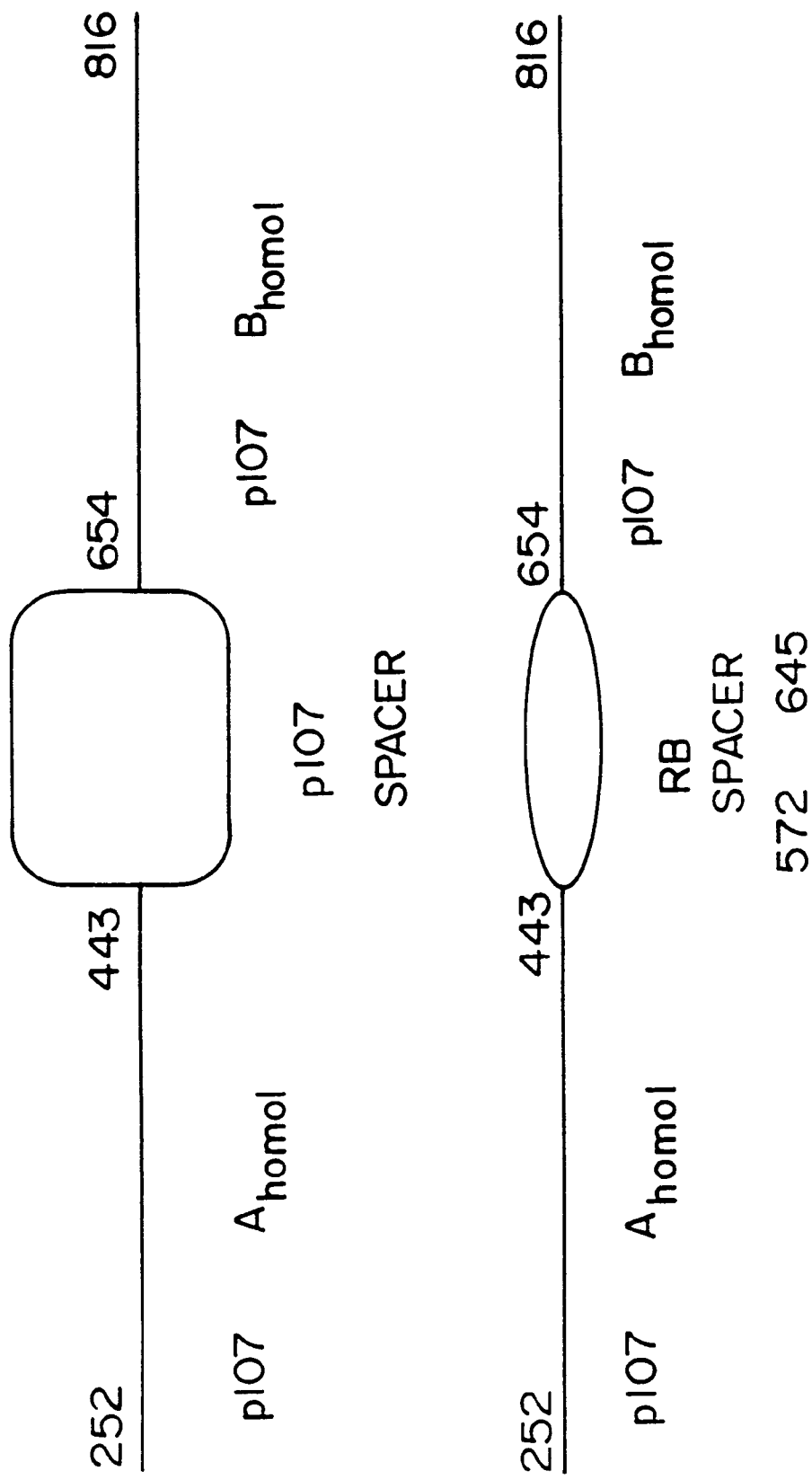

FIG. 3 is a diagram showing (upper) the native p107 pocket region and (lower) a chimeric p107 pocket region in which the RB spacer (RB residues 572–645) is substituted for the p107 spacer between the A and B regions (p107 residues 252–443, 654–816) of the p107 pocket.

Figures 4, 5:
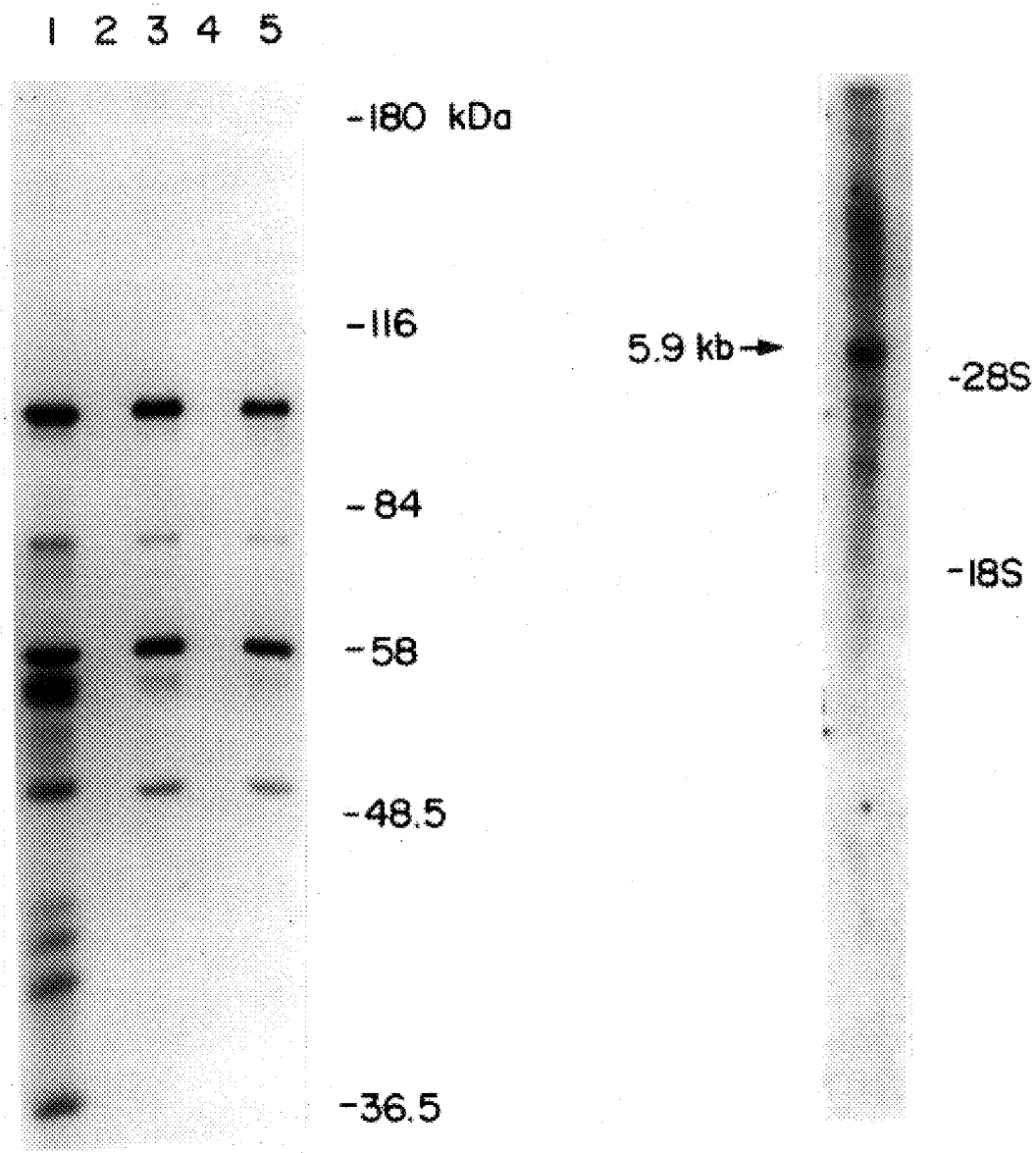

FIG. 4 is a print of a gel showing complex formation between peptide products of transcription-translation of the p107 cDNA of FIGS. 1A–1C and T or E1A. Lane 1, the translation products; lane 2, an M73 immunoprecipitate of the naive translate; to test for binding, the translate was mixed with lysates prepared from: lane 3, 293 cells (containing E1A); lane 4, MEFψK1 cells (containing wild-type T); lane 5, MEFψpPVU-0 cells (containing wild-type T); and immunoprecipitating with the relevant monoclonal antibody, anti-T (PAb419) or anti-E1A (M73). Complexes were separated by electrophoresis in a 7.5% SDS-polyacrylamide gel and detected by fluorography.

FIG. 5 is a print of a gel showing a northern blot of poly-A containing MRNA from 293 cells. 10 μg of poly A RNA, prepared from 293 cells was resolved in a 1% agarose-formaldehyde gel and transferred to nitrocellulose. A 2.8 kb p107 cDNA clone was $^{32}$P labelled and served as the probe.

STRUCTURE

The near full length cDNA for the p107 gene was cloned by first obtaining an internal peptide sequence for peptide p107 and using the internal sequence to design oligionucleotides to screen a cDNA library.

In vitro translates for p107 are able to form a specific complex with viral proteins T and E1A. The peptide maps of authentic protein p107 and the in vitro p107 translate are virtually identical.

Purification of the p107 T and E1A Associated Protein

Generally, p107 was purified by immunoisolation of E1A-p107 complexes, followed by separation of the target antigen in one dimensional SDS polyacrylamide gels, as described in detail below. Briefly, an anti E1A monoclonal antibody, covalently crosslinked to protein A sepharose, was incubated with a lysate prepared from an E1A-producing human cell line, 293 ("293 cells"). The separated proteins in the gel were transferred to nitrocellulose. p107 was visualized by Ponceau S staining prior to excision. From 193 plates (24.5 cm×24.5 cm), approximately 5–7 μg of p107 were purified.

In further detail, cells from approximately fifty confluent plastic plates (24.5 cm×24.5 cm; Nunc) of 293 cells were harvested by scraping into TBS (10 mM Tris-HCl, 150 mM NaCl) and collected by centrifuigation. After removal of the supernatant, cells were lysed in 80 ml of ice cold lysis buffer (50 mM Tris-HCl, pH 8.0, 170 mM NaCl, 0.5% (v/v) NP-40, 10 μg/ml aprotinin [Sigma], phenylmethylsulfonyl-fluoride ["PMSF", Sigma], leupeptin [Boehringer-Mannheim] for 30 min. The lysate was cleared by centrifuigation. The cleared lysate was incubated with approximately 2 ml of MAb M73 (anti E1A, described in Harlow et al., *J. Virol.* 55:533–546, 1985) covalently crosslinked to protein A sepharose (Pharmacia) prepared generally as described in Harlow et al., Cold Spring Harbor Laboratory, 1988; Simanis et al., *Virology* 144:88–100, 1985; Ewen et al., *Cell* 58:257–67, 1989). The mixture was incubated with rocking for 5 hrs at 4° C. Immune complexes were washed first with approximately 350 ml 10 mM Tris-HCl (8.0), 250 mM NaCl, 1 mM EDTA, 0.5% NP-40, and loaded into an empty column. The loaded column was further washed with 10 mM Tris-HCl (8.0), 100 mM NaCl, 1 mM EDTA. Bound protein was eluted from the mAb M73-protein A sepharose column with 100 mM triethylamine, pH about 11, and fractions were collected. Aliquots of the fractions were analyzed by SDS-gel electrophoresis. Peak fractions for the p107 protein were pooled, dialyzed against several volumes of double distilled water at 4° C. The sample was then frozen in dry ice ethanol and lyophilized. The dried samples were resuspended in 62.5 mM Tris-HCl (6.8), 2% SDS, 4M urea, 5% β-mercaptoethanol, 0.01% BPB. The sample was incubated at 37° C. for several hrs, boiled and then spun in a microfuge prior to loading on a gel. After electrophoresis through a 6% gel the proteins were visualized by staining in 0.05% coomassie brilliant blue R-250. The band corresponding to p107 was excised, crushed, and soaked in a small volume of 62.5 mM Tris-HCl, 2% SDS, 5% β-mercaptoethanol for 4 to 5 hrs. The gel fragments were loaded onto a second 8% gel. After electrophoresis, the p107 protein was transferred to nitrocellulose in 25 mM Tris-HCl, 192 mM glycine, 2% methanol, 0.005% SDS, pH 8.3 (as described generally in Aebersold et al., *Proc. Natl. Acad. Sci. USA* 84:6970–74, 1987; Towbin, *Proc. Natl Acad. Sci. USA* 76:4350–54, 1979). Bound protein was stained in 0.1% Ponseau S, 1% acetic acid (Aebersold et al., 1987) for 20 to 30 sec and destained in H$_2$O. The stained p107 band was excised. A total of 193 plates of 293 cells were processed. About 7 μg of purified p107 was obtained. The total area of nitrocellulose used for subsequent protein sequencing was approximately one square cm.

Isolation and Sequence of Peptides

N-terminal sequences of several tryptic peptides of p107 were obtained by automatic sequenation. The peptides were isolated by HPLC after in situ tryptic digestion of gel band purified and blotted p107.

In detail, in situ tryptic digestion of the p107 electroblotted onto nitrocellulose was performed generally as described in Aebersold et al., 1987, omitting the NaOH wash to minimize loss of protein. Sequencing grade bovine trypsin was from Boehringer Mannheim. After digestion the solution was immediately stored at −20° C. until separation of the resultant peptides by narrowbore reverse-phase PHLC was carried out.

Peptides were separated by narrowbore reverse phase HPLC in a Hewlett-Packard 1090 HPLC equipped with a 1040 diode array detector, using a Vydac 2.1 mm×150 mm C4 column. The gradient employed was a modification of that described by Stone et al., *Techniques in protein Chemistry*, Academic Press, Inc., 1989. Briefly, where buffer A was 0.06% trifluoroacetic acid/H$_2$O and buffer B was 0.55% trifluoroacetic acid/acetonitrile, a discontinuous gradient of 5% B at 0 min, 33% B at 63 min, 60% B at 95 min and 80% B at 105 min with a flow rate of 150 μl/min was used. Chromatographic data at 210 nm and 277 nm, and UV spectra from 209 nm to 321 nm of each peak were obtained. While monitoring absorbance at 210 nm, peaks were manually collected into 1.5 ml microfuge tubes and immediately stored without drying at −20° C. in preparation for peptide sequence analysis.

Samples for amino terminal sequence analysis were applied directly to a polybrene pre-cycled glass fiber filter and placed in the reaction cartridge of an ABI Model 477A protein sequencer. The samples were subjected to automated Edmann degradation using a program known as "NORMAL-1", which can be obtained from Bill Lane at the Harvard Microchemistry Laboratory, modified using the manufacturer's recommendations for faster cycle time (37 min) by decreasing dry-down time and increasing reaction cartridge temperature to 53° C. during coupling. The resultant PTH amino acid fraction were manually identified using an on-line ABI model 120A HPLC and Shimadzu CR4A integrator.

Molecular Cloning of the T/E1A Associated p107 Protein

From the partial sequences of three peptides underlined in FIGS. 1A–1C and labeled as NT65, NT85 and NT104, variously long, and moderately degenerate (for NT65) and non-degenerate (for NT85 and NT104) oligonucleotides encoding these three sequences were constructed using the codon utilization tables of Lathe, J. Mol. Biol. 183:1–12, 1985. These oligonucleotides were used to screen a newly generated cDNA library from 293 cells, and a number of cross hybridizing positives were identified. The largest clone isolated was 5.5 kb.

Construction of the cDNA library and screening was carried out as follows. Total cellular RNA was prepared from 293 cells (Maniatis et al., 1982). Poly A RNA was prepared using an oligo dT mRNA purification column (Pharmacia). The poly A RNA was used to construct a directionally cloned cDNA library in UniZap (Stratagene) following the manufacturer's instructions. DNA was packed using Strategene's Gigapack II Gold Packaging extract.

The unamplified library was screened with $^{32}$P-labeled oligonucleotides. From the three peptide sequences NT65 (SEQ ID NO:3): LTAQANVEYNLQQHFEK; NT85 (SEQ ID NO:4): EYEEYVLTVGDFDE; and NT104 (SEQ ID NO:5): VTIPLHGVANDAGEITLIP the following oligonucleotides were respectively constructed:
5' GAGGC(TC)AATGTGGAGTA(TC)AACCTGCAGCAGC A(TC)TTTGAGAA 3' (SEQ ID NO:6); 5' AATTCTCATCAAGTCGCCCACTGTCAG-CACATA CTCCTCATACTCG 3' (SEQ ID NO:7) (the AATT at the 5' end and the G at the 3' end were incorporated into the oligonucleotide to facilitate cloning); and
5' AATTCGGGGATCAGGGTGATCTCGCCAG-CATCATTGGCCAGCCATGC AGGGGGATGGTCACG 3' (SEQ ID NO:8) (the same flanking sequences found in the second oligonucleotide were also engineered into this oligonucleotide).

Filters were hybridized with about 3×10$^6$ cpm/ml for each oligonucleotide in 6× SSC, 5 × Denhardt's, 20 mM NaPO$_4$, 20% formamide, 0.1% SDS and 100 µg/ml denatured, sonicated salmon sperm DNA at 42° C. for 12–18 hrs. Filters were washed in 0.2× SSC at 60° C. and then autoradiographed. Hybridizing phage were plaque purified. The plasmid, pBluescript SK(–), containing the cloned insert, was generated by in vivo excision and recircularization using the purified phage following the protocol provided by Stratagene. This DNA was used for further analysis.

In Vitro Transcription and Translation

Cloned inserts in the pBluescript SK(–) or pBluescript II SK(–) plasmid were used in in vitro transcription reactions using T3 polymerase (Pharmacia). Transcription and translation reactions were performed as described in Kaelin et al., Mol. Cell. Biol. 10:3761–69, 1990.

When used as a template for in vitro transcription-translation, several products were identified. The largest was about 100 kd, and the smallest was about 36 kd, as appears in FIG. 4. Partial proteolytic digests of the 100 kd product and of intact p107 isolated from 293 cells revealed the same pattern of peptide products, indicating that the cDNA template encodes p107 . Moreover, all translation products of greater than 48 kd size bound to T and to E1A but not to a non p107 -binding T mutant, K1T, in immunoprecipitation assays, indicating that the products of this cDNA retain the T/E1A binding activity of the authentic, in vivo-synthesized product. In these gels, authentic p107 migrated just above the 116 kd marker (see, Ewen et al., 1989), suggesting that the 100 kd translation product might be missing certain p107 sequences.

When used as a probe in a northern blotting experiment in which poly A-containing RNA from 293 cells was analyzed, a prominent 5.9 kb RNA species was identified, as FIG. 5 shows. Other less well-defined minor species were also detected. These data are consistent with the major species being a prominent p107 mRNA. Experiments performed on monkey cells indicate that p107 exists as a family of closely migrating bands.

p107 Binding Assays

Binding of in vitro translated p107 to T and to E1A was assayed generally as described for RB. The mouse cell lines MEFψpPV-0 and MEFψK1 (Chen et al. J. Virol. 64:3350–57, 1990) were used as sources of T and K1 respectively. The cell line 293 was used as a source of E1A.

Peptide Map

One dimensional chymotryptic mapping was performed generally as described in Ewen et al. 1989.

PCR Subclone of p107 cDNA

To generate a cDNA of p107 starting at methione 57, an oligonucleotide incorporating a consensus start for translation and p107 sequences (5' GCGCGGATCCGCCACCAT-GATTGGGGATGACTTAG 3' (SEQ ID NO:9)) and an oligonucleotide complementary to the T7 promoter element in pBluescript SK(–) (5' AGTGGGATCCAATACGACTCAC-TATAGG 3' (SEQ ID NO:10)) were used in a PCR reaction. PCR was performed generally as described in Kaelin et al. 1990, except that an annealing temperature of 55° C. was used. The PCR product was digested with BamHI and XhoI and subcloned into pBluescript II SK(–) digested with the same restriction enzymes. The resultant subclone was used for in vitro transcription and translation reactions as described above.

DNA sequencing was performed according to the method described in Sanger et al., Proc. Natl. Acad. Sci. USA 74:5463-67, 1977.

The cDNA sequence and the predicted amino acid sequence of the clone encoding the p107-related 100 kd protein are shown in FIG. 1A–1C. Both strands of subclones of this master cDNA clone were sequenced, and the results were in full agreement. An open reading frame of 2805 bp extends from nt 1 to a stop codon at nt 2806. The same stop codon was found to be present in the same location and confirmed to be functional in three independent p107 clones and by in vitro translation of a truncated cDNA derivative of NT. Several p107 clones shared the same 3' end as determined by restriction analysis, suggesting that it denotes the natural 3' end of the cDNA. Since the distance from the stop codon to the 3' end is 2.7 kb, the gene contains a relatively long 3' untranslated region.

The cDNA segment encoding the 100 kd band is not likely to be a full length p107 cDNA for a number of reasons. The methionine codon at position 57 is not imbedded in a region predicted to be a good consensus start signal (see, Kozak, J. Mol. Biol. 196:947–50, 1987). Translation initiation at methionine 57 resulted in the synthesis of the 100 kd band, and the native protein migrates as a 120 kd band. While the difference in gel migration could be the result of a covalent modification of the latter, translation beginning at methione 57 led to the synthesis of a protein of the predicted size, again suggesting that the 100 kd protein lacks certain N-terminal sequences. In this regard, the sequences 5' to those encoding the methionine at position 57 are completely open and in frame with the p100 product sequence. Moreover, analysis of the codon usage in the region preceding this methionine residue suggests that it is likely to be the coding sequence. Taken together, these data suggest that the largest available clone is nearly, but not entirely, fill length.

In an effort to detect the 5' end of the natural mRNA, a $^{32}$P labeled oligonucleotide complementary to the thirty nucleotides at the 5' end was used as primer for primer extension. The results were consistent with the 5' end of NT being approximately 300 bp from the natural 5' end of the RNA.

Comparison of the p107 Sequence with the RB Sequence

When the predicted amino acid sequence of RB was compared to the available sequences of all proteins in the databases searched, no significant homologies were found (Lee et al., *Science* 235;1394–99, 1987, Friend et al., *Proc. Natl. Acad. Sci. USA* 84:9059–63, 1987). When the predicted amino acid sequence of p107 was compared to available sequence databases (three different gene banks), no significant homologies were found except for the existence of major elements of homology to RB.

Comparisons of the predicted p107 and human and murine RB sequences revealed extensive homology between p107 and both RB species, as shown in FIGS. 2A and 2B. Seven regions of p107 -RB homology were found. Comparing the two proteins linearly in the N to C direction, and referring to FIG. 2A, the first homology region (40% identity) extends from residues 40 to 74 in p107 and 190 to 224 in RB. Then, three closely spaced (the spaces are fewer than 20 residues in length) regions of homology spanning amino acids 252–451 in p107 and covering amino acids 373–579 in RB were detected. The homology ranged from 35–52%, depending upon which region was analyzed. After a gap of about 200 residues in p107 and 60 residues in RB, three additional regions of homology spanning amino acids 648–816 in p107 and amino acids 640–771 in RB were also found. There was a gap of 46 residues between the second and the third region in p107. The corresponding gap in RB was 6 residues. The extent of homology among these three regions ranged from 38% to 62%. The human and mouse RB proteins show 91% identity. Thus, it was not a surprise to note that each of the human RB-human p107 homology regions corresponded precisely to a mouse RB-human p107 homology region. Furthermore, each pair of identical residues detected in p107 and human RB was repeated in the comparison of p107 and mouse RB.

The similarities between p107 and RB are most striking in view of what is known about the functional domain structure of RB. Hu et al.,*EMBO J*. 9:1147–55, 1990, Kaelin et al. and Huang et al. *EMBO J*. 9:1815–22, 1990, have defined the minimal region of RB necessary for T and E1A binding as a colinear region extending from residues 379–793. We have termed it the "pocket" region of the protein (Kaelin et al., 1990, *Cell* 64:521–32, 1991). Two subsegments (A and B) composed of sequences which cannot be invaded by deletion mutagenesis without interrupting T/E1A bending function were also detected (Hu et al., 1990, and Huang et al., 1990). The approximately 75 residue region between them could be invaded, so long as the deleted residues were replaced with other non-specific sequences (Hu et al., 1990). Region A extends from residues 393/394 to 572/571 and Region B from residues 646/649 to 772/773. The p107 homology regions in RB exist almost completely within the RB pocket and correspond closely to both the A and the B regions. They do not overlap the above-noted spacer region, although the p107 homology region extends approximately 20 amino acids N terminal to the upstream boundary of the minimal RB pocket region. Analogous results were noted when the RB homology regions in p107 were mapped. Two segments homologous to the A and B subdomains of RB were noted in p107 but in p107 there is a much larger spacer region noted (about 200 residues in p107, compared to about 60 residues in RB).

At the DNA level, there was little significant homology between RB and p107. Some homology was detected at the 5' ends of the regions encoding segments A and B in both proteins. No stretches of identity greater than six nucleotides were detected.

Chromosome Mapping

A 4.4 kb cDNA clone was used for mapping by in situ hybridization with a digoxygenin-labeled probe. Hybridization procedures were essentially as described in Lawrence, *Cell* 52:51–61, 1988, *Science* 249:928–32, 1990. Analyses were performed on metaphase spreads of normal peripheral blood lymphocytes prepared by standard procedures. Slides were stored at −80° C. and were UV-treated (365 nm) for 1 hr and baked at 65° C. for 4 hrs just prior to hybridization. After rinsing in 1× PBS, slides were denatured in 70% formaldehyde/2× SSC for 2 min at 70° C., and then dehydrated in a graded series to 100% ethanol before air drying. Probe, previously labelled by nick-translation with digoxygenin dUTP (Boehringer), was denatured and combined with the a hybridization solution at a concentration of 5 μg/ml. An excess of human Cot-1 DNA (BRL) was added to compete out hybridization to repetitive sequences, a step found necessary with this cDNA probe.

Following overnight incubation at 37° C., slides were rinsed three times for 30 min each and hybridization detected using anti-digoxygenin antibody directly conjugated to fluorescein (Boehringer). Metaphase chromosomes were identified by banding with DAPI (diaminophenylindole) enhanced by prior incorporation of 5-bromodeoxyuridine into chromosomal DNA.

In some instances simultaneous hybridization to p107 and to the placental tyrosine phosphatase gene (PTP1B) were performed using 2-color detection of bioine and digoxygenin labeled probes. The conditions used for this double-label hybridization are described in Johnson et al. *GATA* 8: In Press, 1990. Use of a dual-band optical filter allowed the two sequences to be visualized simultaneously in precise register with respect to one another.

The RB Homology Region in p107 Constitutes a "Pocket" Domain

In an effort to determine whether the A-Spacer-B region of p107 could operate independently in T-p107 and E1A-p107 binding, appropriate deletion mutants were generated. These proteins were produced by in vitro transcription and translation. Upon mixing with wild type and mutant species of T and with wild type E1A, co-immunoprecipitation of the relevant p107 fragment was sought after adding the relevant monoclonal antibodies.

The segment of p107 extending from one end of the RB homology region to the other bound successfully to T and, to E1A, but not to the K1 mutant of T, which cannot bind either to RB or to p107 in vivo. Therefore, the 225 to 816 region of p107 constitutes an independent T/E1A binding domain, which we term the "p107 pocket".

The spacer region between subdomains A and B in the RB pocket is apparently ephemeral to the T/E1A binding function of this domain. The same is true for the putative p107 spacer. Specifically, the 75 residue RB spacer was substituted for the 205 residue p107 spacer, as shown in FIG. 3, and the resulting chimera was tested for T/E1A binding. The recombined chimaeric p107 segment was apparently as active in T and E1A binding as was the native p107 element. Moreover, the chimaeric p107 segment failed to bind to K1T. Thus, the p107 spacer, as identified by homology analysis, is not essential to at least one function of the p107 pocket, namely, the T/E1A binding function.

The recombined chimaeric p107 segment containing the RB spacer does not bind Cyclin A; the p107 spacer alone does bind Cyclin A.

Thus the in vitro binding studies demonstrate that only a fraction of the p107 primary sequence is necessary for the binding of T and E1A. Though the region in p107 necessary for T and E1A binding has not been mapped, the sequence similarity between the p107 sequences and the region in RB known to be involved in T/E1A binding is striking. The homology spans the two regions A and B defined as the minimal T and E1A binding region in RB as defined by Hu et al., 1990, Huang et al., 1990, and Kaelin et al., 1990. With the exception of the N termini of the A region the boundaries of the homology are fairly well confined to the T/E1A binding regions.

As pointed out above, the sequences between the two regions A and B of the pocket is not critical for T/E1A binding. Some space between the two regions is required, however. It is noteworthy that the spacing of the homology regions in p107 is considerably larger, about 205 amino acids, compared to about 75 amino acids in RB.

The sequence similarity between RB and p107 in the region of the pocket is consistent with the genetic analysis of T/E1A binding and peptide competition studies (De Caprio et a., *Cell* 58:1085–95, 1989; Dyson et al., *Cell* 58:249–55, 1989a; Ewen et al., 1989; Whyte et al., *Cell* 56:67–75, 1989). Moreover, recent evidence strongly suggests that the 300 kd E1A binding protein (Yee et al., *Virology* 147:142–53, 1985; Harlow et al. *Mol. Cell. Biol.* 6:1579–89, 1986) has a similar function. p300 may contain a colinear domain responsible for binding T and E1A that it structurally and functionally related to the RB and p107 pockets.

Every reported naturally occurring mutation in RB maps to the region necessary for T/E1A binding. Furthermore for those tested each fails to bind to T and E1A. Whether this region of RB is a hotspot for recombination or whether such mutations confer a growth advantage to these cells is unknown. Such mutations in the T/E1A binding region of p107 may confer a growth advantage to cells and give rise to human cancer.

In this regard Kaye et al. *Proc. Natl. Acad. Sci. USA* 87:6922–26, 1990 describes a point mutation (706, C→F) in RB isolated from a small cell lung carcinoma which inactivated RB function with respect to phosphorylation, in addition to its ability to bind T/E1A and the cellular proteins identified by Kaelin et al. 1990. This cysteine in RB is within a region of homology between RB and p107, and furthermore this amino acid is conserved between the two proteins in this region. A corresponding C→F mutation in p107 results in a mutant p107 that does not bind T.

An apparently normal p107 is present in the retinoblastoma cell line WERI-1 as well as a number of other Rb- cell lines; WERI-27Rb, SAOS-2 and NCI-H69. Thus, any growth suppression function of p107 is not acting redundantly to the growth suppression function of RB. The sequences of p107 confirms our earlier statement that p107 is not the product of the RB gene (Ewen et al, 1989; Dyson et al, 1989).

In this regard, at least eight cellular proteins can be found in a complex with RB, and the region of RB necessary for binding T or E1A was also responsible for binding to the cellular proteins. The binding of RB to the cellular proteins is capable of being competed for by T peptide, and a variety of RB mutants did not bind to the cellular proteins.

The same set of cellular proteins that have been shown to bind RB also bind p107 . At present it is unclear whether either p107 or RB works upstream or downstream of the cellular proteins in RB mediated growth suppression. The sequence similarity between p107 and RB, the genetics with respect to T/E1A binding, and the fact that peptide replicas can abolish the interactions of p107 and RB with T/E1A and with cellular proteins suggests that the cellular proteins are working upstream of p107 and RB, and suggests that p107 has effector functions different from RB. Alternatively (but apparently unlikely), RB binding to these cellular proteins may not alone be sufficient for it to mediate its growth suppression function. At present we know little about the functions of the sequences outside of the RB pocket which comprise 60% of the protein, and it is noteworthy that some homology exists between portions of the N termini of RB and p107 . Sequences outside the pocket may modulate binding of the cellular proteins to pocket during the cell cycle.

Studies of the phosphorylation status of p107 throughout the cell cycle can provide clues as to when in the cell cycle it exerts its growth suppression function. It has been proposed, on the basis of such studies, that RB may be involved in the G1/S transition or entry into G0. p107 exists in both phosphorylated and unphosphorylated forms, and T (but not E1A) binds only to the unphosphorylated form of p107.

Use

The invention provides for early diagnosis of neoplasm by detection of an absence of wild-type p107 genes, or by detection of the presence of non-wild-type p107 genes, in a tissue sample from the subject, using techniques well-known in the art.

For example, the invention may be used to diagnose tumorigenicity in a tissue sample resulting from point mutations or specific deletions in the p107 gene. Point mutations in the p107 gene sequence may be detected by cloning and sequencing the p107 allele present in tumor tissue. If desired, a polymerase chain reaction technique may be used to amplify the signal of the target gene sequence. Point mutations in the p107 gene sequence may also be detected by cloning the mRNA isolated from tumor tissue to produce cDNA, then sequencing the resultant cDNA, or by sequencing the mRNA directly.

Another method traditionally used to detect point mutations is mismatch detection. This technique uses a labeled riboprobe (sense or antisense) which is complementary to the wild-type p107 gene sequence. The riboprobe is first annealed to either mRNA or DNA isolated from tumor tissue, then cleaved with RNase. The resultant preparation is separated on an electrophoretic gel, and mismatches cleaved by the RNase are detected as smaller segments than the full-length duplex RNA, made up of the riboprobe and p107 mRNA or DNA sequence.

Similarly, mismatches can be detected using DNA probes. Previously identified mutations in the p107 gene may be detected using allele-specific probes containing a gene sequence corresponding to that mutation. Presence of a specific mutation is confirmed when an allele-specific probe hybridizes with DNA sequences from the tumor tissue, which may be amplified using a polymerase chain reaction technique.

Specific deletions of the p107 gene may be detected using restriction fragment length polymorphisms probes, directed at either the p107 gene itself, or nearby marker genes. This invention may be used to detect deletions of the entire p107 gene through the absence of expression products, including p107 mRNA or p107 protein. Loss or mutation of the p107 gene may also be detected through loss of the p107 protein functions, such as loss of the ability to bind SV40 large T antigen. A mutation in the genetic sequence may result in detectable alterations in the p107 protein structure, leading to an inability to bind SV40 large T antigen. Alterations in the p107 protein structure may therefore be detected through binding studies using SV40 large T antigen or monoclonal antibodies.

In addition to tumor tissue, mutations in the p107 gene or protein may be detected in serum, stool, urine, sputum or other body fluids. Diagnostic methods may be designed to employ one or more of these body samples, to detect carcinogenesis at multiple stages. Methods could be designed to detect predisposition to cancer, due to the loss of wild-type p107 alleles. The invention could also be used to facilitate early detection of tumors, or as a means of evaluating the progress of treatment, including chemotherapy and radiotherapy.

The detection of a p107 gene deletion may aid physicians in selecting a course of treatment, based on the presence or absence of the p107 sequence. Because the p107 gene is implicated in the development of a broad range of tumors, it may be used to detect numerous forms of carcinogenesis, including but is not limited to, breast and lung tumors, leukemia and osteosarcomas.

This invention may also be used to a supply p107 gene sequence where the wild-type allele has been mutated or deleted. The wild-type gene may be inserted into a defective cell using vectors well known in the art. If this process is employed, it is preferable to induce recombination of the mutant p107 gene with the wild-type gene in a manner such that the mutant gene is corrected. Alternatively, polypeptides or molecules with p107 activity may be introduced into the defective gene through microinjection to supply the missing wild-type p107 protein product.

The observation that the p107 gene maps to a segment of 20q11.2 suggests a possible specific role for p107 as a tumor suppressing element. Approximately 1–6%, at a minimum, of patients having a neoplastic disease of myeloid cells have a cytogenetically detectable deletion of 20q, as described in Davis et al., *Cancer Genet. Cytogenet.*, 12:63–67, 1984. Yunis et al., *Brit. J. Haematol*, 68:189–94, 1988, reports that the tumor cells from 35% of patients having myelodysplastic syndrome showed a deletion of 20q; approximately 21% of patients having acute myelogenous leukemia also showed this deletion. In the majority of myelodysplastic patients showing the deletion, the deletion has been described as a terminal deletion with variability in the breakpoint within band q11, which results in a loss of all DNA terminal to the breakpoint. Le Beau et al., *Proc. Nat. Acad. Sci., USA*, 82:6692–96, described detecting a smaller, less frequent 20q deletion between breaks at 20 q11.2 and 13.1. Taken together, these data and the similarities between p107 and RB suggest that p107 can play a role in the evolution of one or more neoplastic disorders of myeloid cells. p107 loss may be a relatively frequent event in human tumors, as is true of RB.

Because RB and p107 may exhibit certain redundant finctions, and because a loss of both p107 and RB can be lethal, tumors in which RB function is lost can be expected to have retained p107 function, and vice versa.

We claim:

1. A vector comprising a nucleic acid whose nucleotide sequence includes a region that encodes a polypeptide whose sequence comprises SEQ ID NO:2.

2. A probe comprising a nucleic acid whose nucleotide sequence includes a region that encodes a polypeptide whose amino acid sequence comprises SEQ ID NO:2.

3. An isolated cDNA whose nucleotide sequence includes a region that encodes a polypeptide whose amino acid sequence comprises SEQ ID NO:2.

4. A vector comprising a nucleic acid that encodes a polypeptide comprising residues 225–816 of SEQ ID NO:2.

5. A probe comprising a nucleic acid that encodes a polypeptide comprising residues 225–816 of SEQ ID NO:2.

6. An isolated cDNA that encodes a polypeptide comprising residues 225–816 of SEQ ID NO:2.

7. A vector comprising a nucleic acid whose nucleotide sequence includes a first sequence that encodes a first polypeptide comprising SEQ ID NO:13 and a second sequence that encodes a second polypeptide comprising SEQ ID NO:14, the first and second sequences being separated from one another by a 600 nucleotide spacer, which spacer encodes a polypeptide that binds cyclin A.

8. A probe comprising a nucleic acid whose nucleotide sequence includes a first sequence that encodes a first polypeptide comprising SEQ ID NO:13 and a second sequence that encodes a second polypeptide comprising SEQ ID NO:14, the first and second sequences being separated from one another by a 600 nucleotide spacer, which spacer encodes a polypeptide that binds cyclin A.

9. An isolated cDNA whose nucleotide sequence includes a first sequence that encodes a first polypeptide comprising SEQ ID NO:13 and a second sequence that encodes a second polypeptide comprising SEQ ID NO:14, the first and second sequences being separated from one another by a 600 nucleotide spacer, which spacer encodes a polypeptide that binds cyclin A.

10. A vector comprising a nucleic acid whose nucleotide sequence includes a first sequence that encodes a first polypeptide comprising SEQ ID NO:23 and a second sequence that encodes a second polypeptide comprising SEQ ID NO:25, the first and second sequences being separated from one another by a 588 nucleotide spacer.

11. A probe comprising a nucleic acid whose nucleotide sequence includes a first sequence that encodes a first polypeptide comprising SEQ ID NO:23 and a second sequence that encodes a second polypeptide comprising SEQ ID NO:25, the first and second sequences being separated from one another by a 589 nucleotide spacer.

12. An isolated cDNA whose nucleotide sequence includes a first sequence that encodes a first polypeptide comprising SEQ ID NO:23 and a second sequence that encodes a second polypeptide comprising SEQ ID NO:25, the first and second sequences being separated from one another by a 588 nucleotide spacer.

13. A probe that is identical in nucleotide sequence to a fragment of the cDNA of any one of claims 3, 6, 9, or 12, which fragment is unique to the cDNA in that the fragment is not found in other known cDNAs.

14. A cDNA that is identical in nucleotide sequence to a fragment of the cDNA of any one of claims 3, 6, 9, or 12, which fragment is unique to the cDNA in that the fragment is not found in other known cDNAs.

15. A cDNA that is identical in nucleotide sequence to a fragment of SEQ ID NO:1 and hybridizes specifically to one strand of SEQ ID NO:1 in that, when the fragment is contacted with the strand in the presence of 6× SSC, 5× Denhardt's, 20 mM NaPO$_4$, 20% formamide, 0.1% SDS, and 100 μg/ml denatured, sonicated salmon sperm DNA, at 42° C. for 12–18 hours, the fragment binds to the strand.

16. The cDNA of claim 15, comprising SEQ ID NO;9.

17. A cell transformed with the vector of any one of claims 1, 4, 7, or 10.

18. A cell transformed with a nucleic acid selected from the group consisting of;

(i) nucleic acid whose nucleotide sequence includes a region that encodes a polypeptide whose amino acid sequence comprises SEQ ID NO:2;

(ii) a nucleic acid that encodes a polypeptide comprising residues 225–816 of SEQ ID NO:2;

(iii) a nucleic acid whose nucleotide sequence includes a first sequence that encodes a first polypeptide comprising SEQ ID NO:13 and a second sequence that encodes a second polypeptide comprising SEQ ID NO:14, the first and second sequences being separated from one another by a 600 nucleotide spacer, which spacer encodes a polypeptide that binds cyclin A;

(iv) a nucleic acid whose nucleotide sequence includes a first sequence that encodes a first polypeptide comprising SEQ ID NO:23 and a second sequence that encodes a second polypeptide comprising SEQ ID NO:25, the first and second sequences being separated from one another by a 588 nucleotide spacer.

19. A vector comprising a nucleic acid that encodes a polypeptide comprising a fragment of SEQ ID NO:2, the fragment being selected from the group consisting of SEQ ID NO:3, SEQ ID NO:4, and SEQ ID NO:5.

20. A probe comprising a nucleic acid that encodes a polypeptide comprising a fragment of SEQ ID NO:2, the fragment being selected from the group consisting of SEQ ID NO:3, SEQ ID NO:4, and SEQ ID NO:5.

21. A cDNA that encodes a polypeptide comprising a fragment of SEQ ID NO:2, the fragment being selected from the group consisting of SEQ ID NO:3, SEQ ID NO:4, and SEQ ID NO:5.

22. A vector comprising a nucleic acid whose nucleotide sequence is selected from the group consisting of SEQ ID NO:6, SEQ ID NO:7, and SEQ ID NO:8.

23. A probe comprising a nucleic acid whose nucleotide sequence is selected from the group consisting of SEQ ID NO:6, SEQ ID NO:7, and SEQ ID NO:8.

24. A cDNA whose nucleotide sequence is selected from the group consisting of SEQ ID NO:6, SEQ ID NO:7, and SEQ ID NO:8.

* * * * *